US00PP29174P2

(12) United States Plant Patent
Smith et al.

(10) Patent No.: US PP29,174 P2
(45) Date of Patent: Apr. 3, 2018

(54) DENDRANTHEMA PLANT NAMED 'DAINTY PINK IGLOO'

(50) Latin Name: *Chrysanthemum×morifolium*
Varietal Denomination: Dainty Pink Igloo

(71) Applicants: Mark A. Smith, Fort Myers, FL (US); Cornelis P. Vandenberg, Fort Myers, FL (US)

(72) Inventors: Mark A. Smith, Fort Myers, FL (US); Cornelis P. Vandenberg, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 0 days.

(21) Appl. No.: 15/530,074

(22) Filed: Nov. 30, 2016

(51) Int. Cl.
*A01H 5/02* (2006.01)

(52) U.S. Cl.
USPC ..... Plt./297

(58) Field of Classification Search
USPC ..... Plt./297
See application file for complete search history.

*Primary Examiner* — Annette H Para
(74) *Attorney, Agent, or Firm* — C. A. Whealy

(57) ABSTRACT

A new and distinct cultivar of Dendranthema plant named 'Dainty Pink Igloo', characterized by its upright, outwardly spreading and uniformly mounded plant habit; freely branching habit; dense and full plant form; uniform and freely flowering habit; relatively small button-type inflorescences; light purple-colored ray florets; natural season flowering occurs about September 15 to 23 in Pennsylvania; and good garden performance and winter hardiness.

2 Drawing Sheets

Botanical designation: *Chrysanthemum×morifolium.*
Cultivar denomination: 'DAINTY PINK IGLOO'.

BACKGROUND OF THE INVENTION

The present invention relates to a new and distinct Dendranthema plant, botanically known as *Chrysanthemum×morifolium*, commercially grown as a perennial garden-type Dendranthema plant, and hereinafter referred to by the cultivar name 'Dainty Pink Igloo'.

The new Dendranthema is the product of a planned breeding program conducted by the Inventors in Bogota, Colombia and Smoketown, Pa. The objective of the breeding program is to create new perennial garden-type Dendranthema plants having uniformly mounding plant habit, inflorescences with desirable inflorescence forms, attractive ray and disc floret shapes and colors, winter hardiness and good garden performance.

The new Dendranthema plant originated from a cross-pollination made by the Inventors in 2008 in Bogota, Colombia, of a proprietary seedling selection of *Chrysanthemum×morifolium* identified as code number H3369, not patented, as the female, or seed, parent with a proprietary selection of *Chrysanthemum×morifolium* identified as code number H3746, not patented, as the male, or pollen, parent. The new Dendranthema plant was discovered and selected by the Inventors as a single flowering plant within the progeny of the stated cross-pollination in a controlled greenhouse environment in Smoketown, Pa. on Sep. 27, 2011.

Asexual reproduction of the new Dendranthema plant by vegetative terminal cuttings was first conducted in a controlled greenhouse environment in Smoketown, Pa. in March, 2012 and such asexual propagation has shown that the unique features of this new Dendranthema plant are stable and reproduced true to type in successive generations.

SUMMARY OF THE INVENTION

Plants of the new Dendranthema have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dainty Pink Igloo'. These characteristics in combination distinguish 'Dainty Pink Igloo' as a new and distinct garden-type Dendranthema plant:

1. Upright, outwardly spreading and uniformly mounded plant habit.
2. Freely branching habit; dense and full plant form.
3. Uniform and freely flowering habit.
4. Relatively small button-type inflorescences.
5. Light purple-colored ray florets.
6. Natural season flowering occurs about September 15 to 23 in Pennsylvania.
7. Good garden performance and winter hardiness.

In side-by-side comparisons, plants of the new Dendranthema differ from plants of the female parent selection primarily in ray floret color as plants of the female parent selection have white-colored ray florets. In addition, plants of the new Dendranthema are smaller and have smaller inflorescences than plants of the female parent selection.

In side-by-side comparisons, plants of the new Dendranthema differ from plants of the male parent selection primarily in ray floret color as plants of the male parent selection have darker purple-colored ray florets. In addition, plants of the new Dendranthema are smaller, have smaller inflorescences and flower slightly later than plants of the male parent selection.

Plants of the new Dendranthema can be compared to plants of *Chrysanthemum×morifolium* 'Cool Yoigloo', disclosed in U.S. Plant Pat. No. 20,225. In side-by-side comparisons, plants of the new Dendranthema differ from plants of 'Cool Yoigloo' in the following characteristics:

1. Plants of the new Dendranthema are more compact than plants of 'Cool Yoigloo'.
2. Plants of the new Dendranthema have button-type inflorescences whereas plants of 'Cool Yoigloo' have duplex/decorative-type inflorescences.
3. Plants of the new Dendranthema have smaller inflorescences than plants of 'Cool Yoigloo'.
4. When grown under natural season conditions, plants of the new Dendranthema flower about two to three days earlier than plants of 'Cool Yoigloo'.
5. Plants of the new Dendranthema and 'Cool Yoigloo' differ in ray flower color as plants of 'Cool Yoigloo' have bright red purple-colored ray florets.

BRIEF DESCRIPTION OF THE PHOTOGRAPHS

The accompanying photographs illustrate the overall appearance of the new Dendranthema showing the colors as true as it is reasonably possible to obtain in colored reproductions of this type. Colors in the photographs may differ slightly from the color values cited in the detailed botanical description which accurately describe the colors of the new Dendranthema plant.

The photograph on the first sheet comprises a top perspective view of a typical flowering plant of 'Dainty Pink Igloo' grown in a container.

The photograph on the second sheet is a close-up view of a typical flowering plant of 'Dainty Pink Igloo'.

DETAILED BOTANICAL DESCRIPTION

The aforementioned photographs and following observations and measurements describe plants grown during the early autumn in 25-cm containers in an outdoor nursery in Lancaster, Pa. and under cultural practices typical of commercial garden-type Dendranthema production. During the production of the plants, day temperatures averaged 26.7° C. and night temperatures ranged from 15.6° C. to 18.3° C. Plants were five months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Dainty Pink Igloo'.

Parentage:

*Female, or seed, parent*.—Proprietary selection of *Chrysanthemum×morifolium* identified as code number H3369, not patented.

*Male, or pollen, parent*.—Proprietary selection of *Chrysanthemum×morifolium* identified as code number H3746, not patented.

Propagation:

*Type*.—Vegetative terminal cuttings.

*Time to initiate roots, summer and winter*.—About two weeks.

*Root description*.—Fine, fibrous; typically white in color, actual color of the roots is dependent on substrate composition, water quality, fertilizer type and formulation, substrate temperature and physiological age of roots.

*Rooting habit*.—Freely branching, dense.

Plant description:

*Plant and growth habit*.—Perennial garden-type Dendranthema plant with button-type inflorescences; upright, outwardly spreading and uniformly mounding plant habit; strong and moderately vigorous growth habit.

*Branching habit*.—Freely branching habit, primary lateral branches developing at potentially every node, each primary lateral with multiple secondary and tertiary branches; dense and full plant form; pinching is not required.

*Plant height*.—About 29 cm.

*Plant width*.—About 45 cm.

*Lateral branches*.—Length: About 26 cm. Diameter: About 4.5 mm. Internode length: About 1.25 cm. Strength: Strong. Aspect: Upright to curving upright. Texture: Pubescent, minute; longitudinally ridged. Color: Close to 144A.

*Leaves*.—Arrangement: Alternate, simple. Length: About 2.75 cm. Width: About 1.9 cm. Shape: Obovate. Apex: Cuspidate to mucronate. Base: Attenuate. Margin: Palmately lobed, sinuses between lateral lobes mostly parallel to divergent. Texture, upper and lower surfaces: Pubescent, minute; veins prominent on lower surface. Venation pattern: Pinnate. Color: Developing and fully expanded leaves, upper surface: More green than 147A; venation, close to 146A. Developing and fully expanded leaves, lower surface: More green than 147B; venation, close to 146B. Petioles: Length: About 7 mm. Diameter: About 2 mm. Texture, upper and lower surfaces: Pubescent; minute. Color, upper surface: More green than 147A. Color, lower surface: More green than 147B.

Inflorescence description:

*Type and arrangement*.—Button-type inflorescence form with elongated oblong-shaped ray florets; disc and ray florets arranged acropetally on a capitulum; inflorescences face mostly upright and held above and beyond the foliar plane on strong peduncles.

*Fragrance*.—None detected.

*Flowering response*.—Under natural season conditions, plants flower about September 15 to 23 in Pennsylvania.

*Postproduction longevity*.—Inflorescences maintain good color and substance for about three to six weeks on the plant depending on temperatures; inflorescences persistent.

*Quantity of inflorescences*.—Freely flowering habit with numerous inflorescences developing per lateral branch.

*Inflorescence buds*.—Height: About 5 mm. Diameter: About 5 mm. Shape: Spherical. Color: More green than 147A.

*Inflorescence size*.—Diameter: Relatively small, about 1.5 cm. Depth (height): About 7.5 mm. Disc diameter: About 4 mm. Receptacle diameter: About 3 mm. Receptacle height: About 3 mm.

*Receptacle color*.—Close to 144A.

*Ray florets*.—Quantity and arrangement: About 90 ray florets develop per inflorescence and arranged in five to seven whorls. Length: About 7 mm. Width: About 2.5 mm. Shape: Elongated oblong. Apex: Acute or emarginate. Base: Attenuate and then fused into a short tube. Margin: Entire. Orientation: Initially upright, then horizontal. Texture, upper and lower surfaces: Smooth, glabrous; longitudinally ribbed. Color: When opening, upper surface: Close to N74A; at the base, close to 144A. When opening, lower surface: Close to 75B to 75C. Fully opened, upper surface: Close to 75A; at the base, close to 144A; color becoming closer to 75B with development. Fully opened, lower surface: Close to 75C; color becoming closer to 75D with development.

*Disc florets*.—Quantity and arrangement: About 24 fused disc florets develop per inflorescence and massed at the center of the capitulum. Length: About 4 mm. Diameter: About 1 mm. Shape: Tubular, elongated. Apex: Five-pointed. Texture, inner and outer surfaces: Smooth, glabrous. Color, mature: Apex: Close to 12A. Mid-section: Close to 144A. Base: Close to NN155D.

*Phyllaries*.—Quantity and arrangement: About twelve phyllaries develop per inflorescence and arranged in a single whorl. Length: About 6 mm. Width: About 2.5 mm. Shape: Lanceolate. Apex: Acute. Base: Truncate. Margin: Entire; membraneous. Texture, upper surface: Smooth, glabrous. Texture, lower surface: Pubescent, minute. Color, upper surface: Close to 146A. Color, lower surface: More green than 147A.

*Peduncles*.—Length, terminal peduncle: About 3.5 cm. Length, third peduncle: About 5 cm. Diameter, terminal peduncle: About 1.5 mm. Angle: Mostly upright or curving upright. Strength: Strong, wiry. Texture: Pubescent; minute. Color: Close to 146A.

*Reproductive organs*.—Androecium (present on disc florets only): Stamen number: Five per floret. Filament length: About 3 mm. Filament color: Close to 150D. Anther length: Less than 1 mm. Anther shape: Narrowly oblong. Anther color: Close to 12A. Pollen amount: None observed. Gynoecium (present on ray and disc florets): Pistil length: About 4 mm. Stigma shape: Bi-parted. Stigma color: Close to 9A. Style length: About 3 mm. Style color: Close to 9A. Ovary color: Close to 145D.

*Seeds and fruits*.—Seed and fruit production has not been observed on plants of the new Dendranthema.

Disease & pest resistance: Resistance to pathogens and pests common to Dendranthema plants has not been observed on plants of the new Dendranthema grown under commercial production conditions.

Garden performance & temperature tolerance: Plants of the new Dendranthema have demonstrated excellent garden performance, are hardy to USDA Zone 5 and tolerate high temperatures about 37.8° C.

It is claimed:

1. A new and distinct Dendranthema plant named 'Dainty Pink Igloo' as illustrated and described.

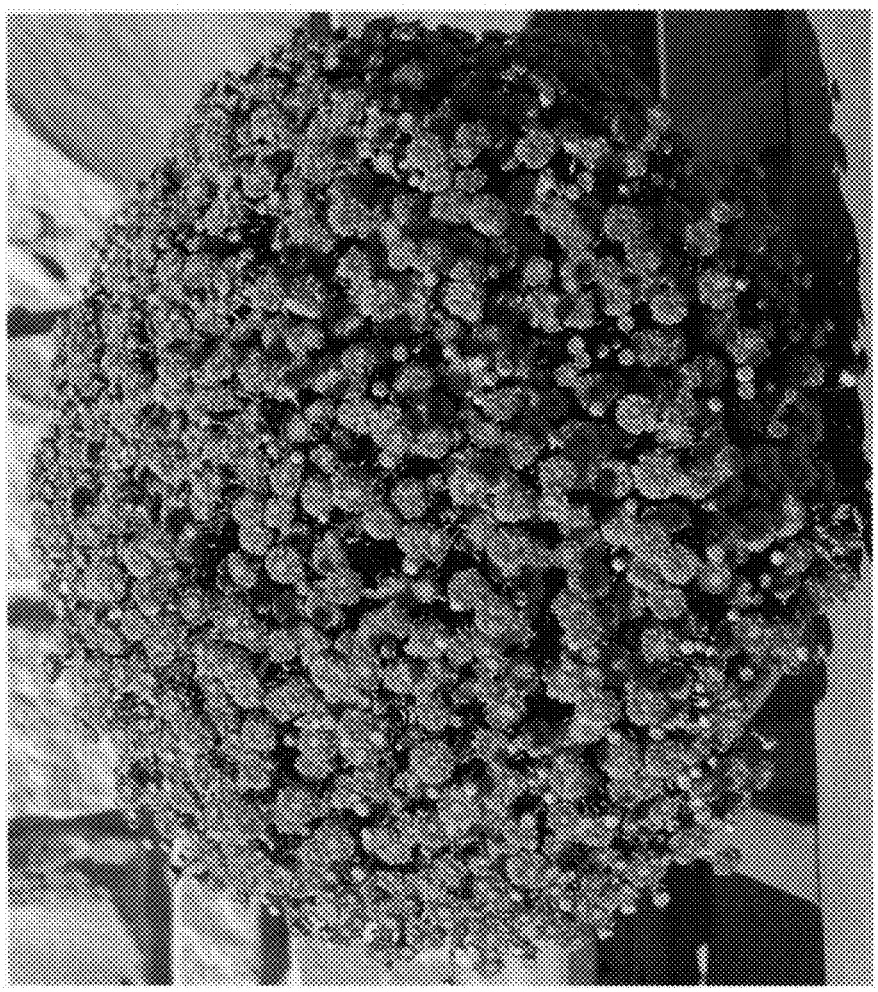

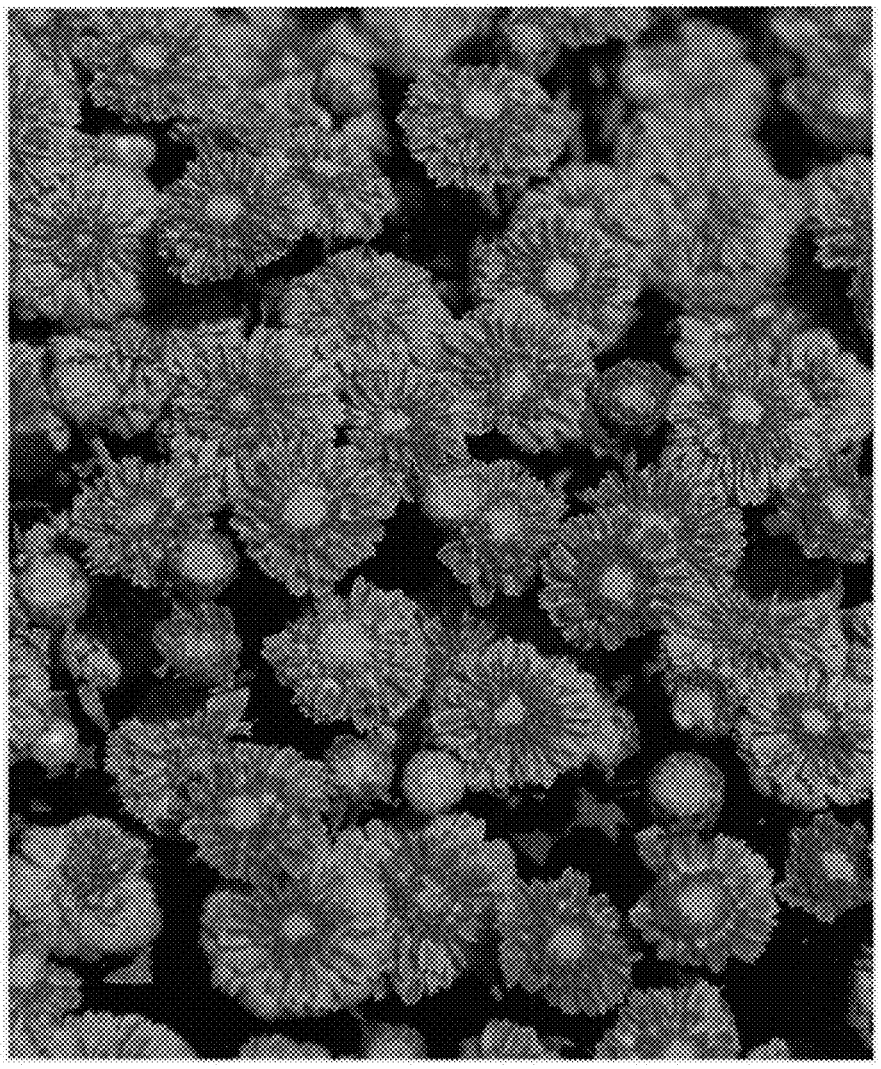

* * * * *